United States Patent [19]

Capuder

[11] Patent Number: 5,985,625

[45] Date of Patent: *Nov. 16, 1999

[54] PROCESS FOR THE ISOLATION OF CLAVULANIC ACID AND OF PHARMACEUTICALLY ACCEPTABLE SALTS THEREOF FROM THE FERMENTATION BROTH OF STREPTOMYCES SP. P 6621 FERM P 2804

[75] Inventor: Egidij Capuder, Dob, Slovenia

[73] Assignee: Lek Pharmaceutical & Chemical Co. dd, Ljubljana, Slovenia

[ * ] Notice: This patent is subject to a terminal disclaimer.

[21] Appl. No.: 09/113,790

[22] Filed: Jul. 10, 1998

Related U.S. Application Data

[63] Continuation of application No. 08/632,402, Apr. 10, 1996, Pat. No. 5,780,274.

[30] Foreign Application Priority Data

Mar. 2, 1994 [SI] Slovenia ............................ P-9400107

[51] Int. Cl.⁶ .............................. C12P 17/14; C12P 17/16
[52] U.S. Cl. ...................... 435/119; 435/118; 435/120; 435/886; 435/41; 435/71.3; 540/349
[58] Field of Search ..................... 435/118, 119, 435/120, 886, 41, 71.3, 117; 540/349

[56] References Cited

U.S. PATENT DOCUMENTS

| | | | |
|---|---|---|---|
| 3,873,425 | 3/1975 | Kobayashi et al. | 435/145 |
| 4,140,764 | 2/1979 | Howarth | 424/114 |
| 4,148,880 | 4/1979 | Celmer et al. | 424/119 |
| 4,427,690 | 1/1984 | Cole et al. | 514/210 |
| 4,886,602 | 12/1989 | Kuehne et al. | 210/637 |
| 4,956,180 | 9/1990 | Cassani et al. | 424/118 |
| 5,268,283 | 12/1993 | Mothes et al. | 435/144 |
| 5,310,898 | 5/1994 | Copar | 540/349 |
| 5,422,256 | 6/1995 | Cooper et al. | 435/128 |

FOREIGN PATENT DOCUMENTS

| | | |
|---|---|---|
| 0 385 552 | 9/1990 | European Pat. Off. . |
| 0 431 679 | 12/1991 | European Pat. Off. . |
| 0 562 583 | 9/1993 | European Pat. Off. . |
| 60-70092 | 4/1985 | Japan . |
| 4-75596 | 3/1992 | Japan . |
| 4-295494 | 10/1992 | Japan . |
| 172021 | 4/1995 | Poland . |
| 1508977 | 4/1978 | United Kingdom . |
| 1563103 | 3/1980 | United Kingdom . |
| 1578739 | 11/1980 | United Kingdom . |
| 93/25557 | 12/1993 | WIPO . |
| 94/22873 | 10/1994 | WIPO . |

OTHER PUBLICATIONS

Derwent WPI, Week 8109, Accession No. 81–14362D (Derwent abstract of Japanese Patent Kokai No. 55–162,993, Dec. 19, 1980).

*Ullmann's Encyclopedia of Industrial Chemistry*, VCH Publishers, New York, NY, 1990, vol. A16, pp. 194–195.

A.M.A. Nabais et al., "Ultrafiltration of fermented broths and solvent extraction of antibiotics", *Bioprocess Engineering*, 13, 215–221 (1995).

Schweitzer, *Handbook of Separations for Chemical Engineers*, 2nd edition, McGraw–Hill, New York, 1988, Section 2.1 "Membrane Filtrattion", pp. 2.1–2.103.

Belter et al., *Bioseparations: Downstream Processing for Biotechnology*, John Wiley & Sons, New York, 1988, pp. 1–17, 39–75, 237–255.

Noble and Stern, *Membrane Separations Technology: Principles and Applications*, Elsevier, Amsterdam, 1995, Chapter 8, pp. 353–413.

Mackay and Salusbury, "Choosing between centrifugal and crossflow microfiltration", *The Chemical Engineer*, Apr. 1988, pp. 45–50.

Michaels and Matson, "Membranes in biotechnology: state of the art", *Desalination*, v.53 (1985), 231–258.

*Primary Examiner*—Leon B. Lankford, Jr.
*Assistant Examiner*—Christopher R. Tate
*Attorney, Agent, or Firm*—Heller Ehrman White & McAuliffe

[57] ABSTRACT

A process for the isolation of clavulanic acid pharmaceutically acceptable salts thereof, such as potassium clavulanate, from the aqueous fermentation broth of a clavulanic acid-producing microogranism comprises the microfiltration of the broth without prior treatment.

17 Claims, No Drawings

PROCESS FOR THE ISOLATION OF CLAVULANIC ACID AND OF PHARMACEUTICALLY ACCEPTABLE SALTS THEREOF FROM THE FERMENTATION BROTH OF STREPTOMYCES SP. P 6621 FERM P 2804

CROSS-REFERENCE TO RELATED APPLICATIONS

This application is a continuation of, and claims the benefit under 35 USC 120 of, application Ser. No. 08/632,402, filed Apr. 10, 1996 now U.S. Pat. No. 5,780,274. application Ser. No. 08/632,402 in turn is a 371 of PCT International Application No. PCT/SI65/00002, filed Feb. 23, 1995, which claims the benefit under 35 USC 119 Slovenian Application No. P-9400107, filed Mar. 2, 1994.

TECHNICAL FIELD
(IPC C 12 P 17/18, C 07 D 498/04)

The present invention belongs to the field of pharmaceutical industry and relates to a novel and improved process for the isolation of clavulanic acid and of pharmaceutically acceptable salts thereof from the fermentation broth of Streptomyces sp. P 6621 FERM P 2804. 4

TECHNICAL PROBLEM

There exists a constant need for a novel and improved process for preparing pure clavulanic acid and pharmaceutically acceptable salts thereof such as potassium clavulanate by the isolation from the fermentation broth obtained by means of a clavulanic acid-producing microorganism, in which process sophisticated conventional isolation methods and chromatographic purification of the desired product would be avoided.

PRIOR ART

Clavulanic acid is the common name for (2R,5R,Z)-3-(2-hydroxyethylidene)-7-oxo-4-oxa-1-azabicyclo[3.2.0]heptane-2-carboxylic acid of the following formula

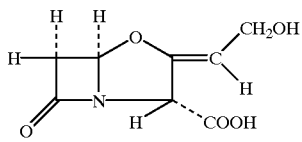

Alkali metal salts and esters thereof-are active as inhibitors of beta-lactamases produced by some Gram positive as well as some Gram negative microorganisms.

In addition to the action of inhibiting beta-lactamases, clavulanic acid and alkali metal salts thereof also have a synergistic action in combination with beta-lactam antibiotics of penicillin and cephalosporin series. Therefore clavulanic acid and salts thereof are used in galenic preparations to prevent the deactivation of beta-lactam antibiotics. Commercial preparations contain a more stable potassium salt of clavulanic acid (the acid alone is rather unstable) in combination with amoxicillin trihydrate.

Clavulanic acid is prepared by the fermentation of a clavulanic acid-producing microorganism such as various microorganisms belonging to different Streptomyces strains such as S. clavuligerus NRRL 3585, S. jumoninensis NRRL 5741, S. katsurahamanus IFO 13716 and Streptomyces sp. P 6621 FERM P 2804.

The aqueous culture broth obtained after fermentation may be purified and concentrated according to conventional processes comprising e.g. filtration and chromatographic purification as illustrated in GB 1,508,977 prior to the extraction of the aqueous solution with the organic solvent to obtain a solution of impure clavulanic acid in an organic solvent.

GB 1,508,977 teaches, inter alia, that salts of clavulanic acid may be obtained by the adsorption of the clavulanate anion in the filtered broth onto an anionic exchange resin and are eluted therefrom with an electrolyte, the solution formed is desalted and then the solvent is removed. This process may be used to achieve acceptable yields of the desired substance, yet it requires sophisticated purifications by chromatographic methods and the use of resin columns demands important investments, which limits production operations on a large scale.

GB 1,543,563 discloses a modified fermentation process using the strain S. clavuligerus NRRL 3585, wherein the pH value of the medium is maintained in the range between 6.3 and 6.7 and thus the yield of the desired compound increases. Salts of clavulanic acid such as potassium clavulanate are prepared by re-salting from lithium clavulanate, whereby the desired compound is also purified.

EP-A-0 026 044 illustrates the use of tertbutylamine salt of clavulanic acid as a useful intermediate in the preparation of clavulanic acid. The salt is known from BE 862 211, but only as an ingredient in pharmaceutical formulations.

EP-B-0 182 522 discloses a method of preparing clavulanic acid by the fermentation of microorganism S. clavuligerus. An important improvement of the process was achieved by the addition of a carbon source such as glycerol into the fermentation medium in the course of the process either continually or intermittently, whereat it is very important that the carbon level is maintained in a sufficiently low concentration, namely under 0.5% (w/v) and by no means exceeds 2%. The Examples illustrate that the essential improvement of the increased yield of clavulanic acid was observed when the carbon source was added during fermentation. It is stated that the concentration of clavulanic acid in t fermentation broth after 160 hours was about 1400 μg/ml, this being a noticeable improvement over previous processes.

A further improvement was also a novel process of purifying clavulanic acid from solution as its lithium salt. However, to achieve a higher purity of lithium clavulanate a concentrated solution of another lithium salt such as lithium chloride was added. The obtained recrystallized lithium clavulanate could be further purified and then optionally converted into other salts such as potassium clavulanate, in a manner known from the above literature.

The mycelium, proteins and other solids are removed by known methods such as centrifugation or filtration with a possible prior treatment of the fermentation broth with a selected aggregation agent to aggregate the mycelium and thus make possible an easier filtration. The filtered fermentation broth is further treated with ion exchange resins or by precipitation with a solvent such as acetone in order to remove proteins and the precipitate is separated by repeated centrifugation and filtration. This separation of the mycelium, proteins and other accompanying particles in the suspension originally present in the fermentation broth, is time-consuming and requires several working steps.

These time-consuming methods of removing the mycelium, proteins and other suspended particles and subsequent isolation from the obtained transparent fermentation broth as well as preparation of pure clavulanic acid and salts thereof were avoided in a manner as disclosed in the published EP-A-0 385 552 and EP-A-0 387 178.

The whole process comprises three steps, i.e. purifying the fermentation broth of the mycelium, proteins and other solid particles, purifying the clavulanic acid present in an impure form in the broth of a purified filtrate of *Streptomyces clavuligerus* by using one of the primary, secondary or tertiary amines forming stable intermediary salts of clavulanic acid, whereby the major part of accompanying impurities in clavulanic acid are separated, and as the last step, the conversion of intermediary amine salts of clavulanic acid (of 85% purity) into the desired alkali metal salt such as potassium clavulanate.

The first step is disclosed in more detail in EP-A-0 385 552, wherein from the aqueous culture broth obtained by the fermentation of the microorganism *Streptomyces clavuligerus*, by means of a physico-chemical process of coagulation-flocculation, the mycelium, proteins and other solid particles are removed. The flocculi obtained in this process are sufficiently large and compact so that an easy sedimentation and separation is made possible, which is best achieved by using rolling sieves. Thus a transparent broth is obtained, which may be optionally concentrated by reverse osmosis.

In this manner a purified fermentation broth is obtained, the conventional purifying methods such as centrifugation, adsorption on active carbon, filtration with coadjuvants etc. having been avoided.

In all known processes it is also necessary (which is different from the disclosed flocculation method) that the purified broth of the culture is treated by means of various processes of deproteinization and ion exchange, which causes significant total losses in the final yield of the desired substance. In contrast to well-known methods, the total yields in the flocculation method amount to 85 to 90%.

The disclosed method of coagulation-flocculation from the fermentation broth of *Streptomyces clavuligerus* is based upon adding an inorganic electrolyte into the broth culture to increase the coagulant action, applying the inorganic coagulant as initiator of the coagulation process under stirring and at a pH value of the medium between 6 and 8, adding an organic electrolyte when the flocculation begins, and then separating the obtained flocculi from the fermentation broth using rolling sieves or filtration and, optionally, when flocculation takes place in the presence of a water-immiscible solvent, decanting the phases, separating the flocculi and, optionally, concentrating the liquid by reverse osmosis or evaporation.

EP-A-0 562 583 discloses the use of salts of clavulanic acid with organic diamines such as N,N'-diisopropylethylenediammonium diclavulanate as useful intermediates for the isolation and preparation of pure clavulanic acid or alkali metal salts thereof such as potassium clavulanate from ethyl acetate extract obtained after the solvent extraction of the obtained aqueous culture broth formed after fermentation, wherein clavulanic acid is present.

TECHNICAL SOLUTION

The aim of the invention is to improve the process of isolation of clavulanic acid from the fermentation broth obtained by means of a clavulanic acid-producing microorganism such as Streptomyces sp. P 6621 FERM P 2804, in which process time-consuming conventional method of removing the mycelium, proteins and other suspended solid particles present in the aqueous culture broth would be avoided, followed by the preparation of salts of high purity such as potassium clavulanate.

Suitable salts according to the present invention are pharmaceutically acceptable alkali metal and alkaline earth metal salts such as sodium, potassium, calcium and magnesium salts. Among these salts sodium and potassium salt, especially potassium salt are the most suitable.

The present invention is generally useful for purifying fermentation broths obtained by means of a clavulanic acid-producing microorganism.

It is evident from the above Prior Art that known processes have comprised time-consuming isolation methods and only EP-A-0 385 552 discloses an improved process, wherein a completely transparent broth is obtained. However, it is a disadvantage of this process that, in order to achieve the desired aim, several reagents such as inorganic electrolytes, coagulants, organic polyelectrolytes have to be used and that flocculation, sedimentation or filtration of the fermentation broth require a relatively long production time, which affects the purity of the desired product On page 2, column 2, lines 22 to 35, some possibilities of purifying the fermentation broth are given, yet said methods would lead to a significant decrease of the yield of clavulanic acid. It is further stated that the use of several sophisticated techniques in the process of isolation and purification such as ultrafiltration and reverse osmosis would not simplify the process because the use of those methods would require prior filtrations on active carbon or ionic resins.

Contrary to these statements it has surprisingly been found that it may be possible to avoid the use of several reagents as used in the process disclosed in EP-A-0 385 552, as well as other time-consuming ways of purification of the aqueous fermentation broth, which ways are disclosed in the literature, when according to the present invention a microfiltration method is used, wherein the mycelium, a major part of proteins (at least 80% of those present in the broth) and other suspended particles are removed.

To this purpose there a multi-stage device for continuous microfiltration is used, which makes possible to carry out the process of separating the mycelium and aqueous filtrate in a dwell time of less than half an hour, the device being composed of several (five) serially connected independent segments (filtration loops). Each segment has its own circulation pump which permits the desired velocity of the fermentation broth (5 to 8 m/s) through channels of ceramic filtering elements having a pore size of 0.05 μm. In the microfiltration process taking place at a temperature between about 20° C. and 40° C. (the temperature should not exceed 40° C.), tangentional velocities are regulated in such a way that in a solid fraction the molecules of a molecular weight over 30,000 are retained. In such a way we succeeded in removing about 80 to 90% of the proteins present. The mycelium separated in the microfiltration process was also washed with water in order to increase the yield of clavulanic acid in the combined filtrate. By the disclosed method of purifying the aqueous fermentation broth by microfiltration, over 95% of clavulanic acid are retained in the purified aqueous phase, which even exceeds the results of the flocculation method of EP-A-0 385 552 and represents a further improvement of the present invention.

After microfiltration the filtrate may be optionally purified by an ultrafiltration process. The purpose of that purification is to separate a major part of the remaining protein impurities and other accompanying impurities having a higher molecular weight than clavulanic acid. In such a way undesired impurities are successfully removed, which may precipitate upon extraction with a water-immiscible organic solvent, whereby the colouring of the aqueous filtrate obtained after purification with microfiltration is essentially reduced and the purity of the desired product is further improved.

In the ultrafiltration device a polymeric membrane having a high resolution rate of about 20,000 daltons (between 10,000 and 30,000 daltons) is used. The process is carried out continuously so that the dwell times are as short as possible, and over two serially connected ultrafiltration devices (which increases the separation selectivity of impurities and clavulanic acid); by adding pure washing water as well as by counter-current conveying of the retentate (aqueous phase) obtained in the ultrafiltration process, the losses of clavulanic acid in the aqueous phase are reduced to less than 5%.

The combined aqueous filtrate is then concentrated in a reverse osmosis device at a temperature about room temperature to about ⅕ of the original volume to obtain a concentrated aqueous phase of impure calvulanic acid and then the obtained concentrate (retentate) is directly extracted at temperatures between 15° C. and 25° C. (extraction may also take place at a temperature under 15° C.) with a water-immiscible organic solvent such as ethyl acetate, in an acidic medium in the pH range of the medium between 1 and 3, which is adjusted by adding inorganic acid such as sulfuric acid. Besides ethyl acetate, also other water-immiscible organic solvents may be used such as methyl acetate, methyl isobutyl ketone or n-butyl alcohol.

Since by the microfiltration process we succeeded to remove the mycelium and a major part of the proteins present, a direct extraction of the purified and concentrated aqueous fermentation broth with an adequate water-immiscible organic solvent such as ethyl acetate is possible without the use of time-cosuming purification methods as applied in known ways disclosed in the above literature and there is avoided the use of additional reagents as applied in the coagulation-flocculation method for the purifying of the fermentation broth. Thus, in addition to the above improvement, the process according to the invention also provides a reduction of costs of the method of broth purification. To avoid a denaturation of the remaining proteins in the aqueous phase concentrate because of an interaction with the organic solvent or sulfuric acid in the course of the extraction of the impure clavulanic acid from the aqueous phase into the organic phase, it is best to carry out the extraction in a series of centrifugal extractors, wherein in one of them, namely in a self-emptying centrifugal separator, the separated proteins are removed simultaneously and continuously.

In the obtained extract of the impure clavulanic acid in a water-immiscible organic solvent there may be also present water-soluble impurities such as various decomposition products of clavulanic acid that are more polar than clavulanic acid alone, hence water-soluble impurities are removed by washing the combined organic phase with water. In this manner a purified extract of clavulanic acid in organic phase such as ethyl acetate extract is obtained.

Clavulanic acid may be isolated from the organic phase and purified so as disclosed in the process of our EP-A-0 562 583. The best way of isolating clavulanic acid as described in this patent application is carried out by a reaction of the ethyl acetate extract of the clavulanic acid with N,N'-diisopropylethylenediamine at a temperature of about room temperature and by a subsequent conversion of the obtained intermediary N,N'-diisopropylethylenediammonium diclavulanate with potassium 2-ethyl hexanoate in an aqueous isopropanol solution and at room temperature to obtain potassium clavulanate, which is isolated with a high purity.

Now it has been found that the preparation of the intermediary N,N'-diisopropylethylenediammonium diclavulanate is best carried out in such a way that in the reaction between a water-immiscible organic phase such as ethyl acetate extract of the clavulanic acid and N,N'-diisopropylethylenediamine there is used an organic phase wherefrom water has been completely removed since already small water amounts may disturb the preparation of the intermediary salt as the separated salt dissolves in the water present in the organic phase and pitched by-products may be obtained, which makes the drying more difficult.

If water is completely removed from the organic phase, the stability of the organic phase or of the extract increases since it is well-known that the stability of clavulanic acid in aqueous solutions and in an acidic pH medium in the extraction process is very poor. Therefore for the drying of the organic phase such as ethyl acetate extract of clavulanic acid, drying in a rectification column (principle of fractional distillation) in vacuo was used because of the poor stability of the intermediary salt at higher temperatures. It is an essential feature of this method that the organic phase such as ethyl acetate and water form an azeotrope having a minimum boiling point and thus the organic phase such as ethyl acetate extract is completely dried in the disclosed manner. Thus the organic phase such as ethyl acetate extracts always has a water content of less than 0.1 vol. %, averagely from 0.03 to 0.05 vol. %. The completely anhydrous organic phase such as ethyl acetate extract of clavulanic acid is then, within a very short dwell time, concentrated by evaporation to a ¹⁄₂₀ of the original volume to be subsequently reacted with N,N'-diisopropylethylenediamine.

The subsequent reaction of N,N'-diisopropylethylenediammonium diclavulanate with potassium 2-ethyl hexanoate to potassium clavulanate of high purity may be carried out as disclosed in our EP-A-0 562 583 and best in such a way as disclosed in the Examples and illustrated by the above improvements.

The invention is illustrated but in no way limited by the following Examples.

EXAMPLE 1

Continuous preparation of a concentrate of ethyl acetate extract containing impure clavulanic acid An aqueous fermentation broth (10,000 l) obtained by the fermentation of the microorganism Streptomyces sp. P 6621 FERM P 2804 (concentration of clavulanic acid amounted to 3580 mg/l) was added to a 33% aqueous solution (5 l) of sulfuric acid in a vessel (capacity 50 m$^3$) under stirring and cooling so that the pH value of the medium was maintained between 5.8 and 6.2. Then the broth was continuously added to a microfiltration device with a flow rate of 1200 l/h, which device was composed of five serially connected segments. Each segment had its own circulation pump to provide for the velocity the fermentation broth through the channels of ceramic filtering elements with a pore size of 0.05 µm to be 8 mls. By the microfiltration process, wherein care was taken that the temperature did not exceed 40° C., the mycelium and a major part of proteins and of other suspended solid particles were removed.

The separated solids were washed with water having the flow rate of 300 l/h and then the combined filtrate (permeate) after microfiltration was added continuously with the flow rate of 1500 l/h into a reverse osmosis device, wherein the permeate was concentrated to ⅕ of the original volume.

To the concentrate (retentate) obtained after the reverse osmosis with a flow rate of 300 l/h, a 33% aqueous solution (4 l/h) of sulfuric acid was added so that the pH value of the medium was maintained between 1.5 and 2.0, then ethyl acetate was added at a flow rate of 900 l/h to extract an acidic retentate at room temperature in the countercurrent in a series of five centrifugal extractors, whereat in the second—self-emptying—centrifugal separator the still remaining separated proteins were simultaneously removed.

The combined ethyl acetate extract from the series of the centrifugal extractors was washed in the first centrifugal extractor with demineralized water having a flow rate of 30 l/h and thus the still remaining water-soluble impurities were removed. The ethyl acetate extract having the flow rate of 900 l/h was dried in vacuo at the temperature of 30° C. in the rectification column so that the water content of 0.03 vol. % was achieved, then the extract was evaporated in a thin-layer evaporator in vacuo at the temperature of 30° C. to a $\frac{1}{20}$ of the original volume. The obtained concentrated ethyl acetate extract (concentration of the impure clavulanic acid amounted to 50 g/l) having the flow rate of 45 l/h was decolourized by a continuous addition of active carbon (0.45 kg), the mixture was stirred for 30 minutes and then the carbon was filtered off from the suspension of the concentrate of the ethyl acetate extract on a pressure filter under nitrogen pressure of 1 bar to obtain a dry concentrate (45 l) of the ethyl acetate extract containing impure clavulanic acid.

EXAMPLE 2

Preparation of N,N'-diisopropylethylenediammonium diclavulanate

To a dry concentrate (45 l) of ethyl acetate extract obtained in the continuous process of Example 1 (the clavulanic acid content amounted to 50 g/l), N,N'-diisopropylethylenediamine (1.41) was added for 5 minutes under vigorous stirring at the temperature of 25° C. The obtained suspension was filtered off, the obtained crystals were resuspended in acetone (45 l) and, at stirring and cooling the suspension at a temperature under 10° C., crystals of the desired substance were separated, which crystals were filtered off, washed with acetone and dried in vacuo at the temperature of 30° C. Crystals of N,N'-diisopropylethylenediammonium diclavulanate (3.3 kg; the clavulanic acid content amounted to 60%) were obtained.

EXAMPLE 3

Preparation of potassium clavulanate

N,N'-diisopropylethylenediammonium diclavulanate (3.3 kg) from Example 2 was dissolved in an isopropanol/water mixture (82.5 l; the water portion amounted to 1.5%) and to the obtained solution active carbon (1.5 kg) and potassium 2-ethyl hexanoate (0.5 l; 2 M) were added for 30 minutes under stirring at room temperature. Then the carbon and the obtained precipitate were filtered off. To the obtained filtrate (80l) a solution (6 l) of potassium 2-ethyl hexanoate (2 M) in isopropanol was added for 20 minutes during stirring at room temperature. The obtained suspension was then stirred under cooling at a temperature between 0° C. and 5° C. for another 2 hours, then the separated crystals were filtered off, washed with isopropanol and acetone and dried in vacuo at the temperature of 30° C. Potassium clavulanate (2 kg; USP grade, the clavulanic acid content 80.6%, determined by HPLC method) was obtained.

I claim:

1. A process for the isolation of potassium clavulanate from an aqueous fermentation broth of a clavulanic acid-producing microorganism, the process comprising the steps of:

(a) continuous microfiltration of the broth, thereby producing a microfiltration filtrate containing the clavulanic acid;

(b) optionally ultrafiltering the microfiltration filtrate to produce an ultrafiltration filtrate containing the clavulanic acid;

(c) concentrating the microfiltration filtrate from step (a) or the ultrafiltration filtrate from step (b) by reverse osmosis, thereby producing a retentate containing the clavulanic acid;

(d) extracting the retentate with a water-immiscible organic solvent, thereby producing an organic phase containing the clavulanic acid;

(e) drying the organic phase;

(f) reacting the clavulanic acid in the organic phase with N,N'-diisopropylethylenediamine, thereby producing a salt of N,N'-diisopropylethylenediamine with clavulanic acid;

(g) reacting the salt of N,N'-diisopropylethylenediamine with clavulanic acid with a potassium salt, thereby producing potassium clavulanate; and (h) isolating the potassium clavulanate.

2. The process of claim 1 where the microfiltration is carried out at a broth pH between 5.8 and 6.2.

3. The process of claim 1 where the microfiltration is carried out at a broth temperature between 20° C. and 40° C.

4. The process of claim 1 where the microfiltration is continuous microfiltration through filter elements having a pore size of 0.05 μm.

5. The process of claim 1 where optional step (b) comprises continuous ultrafiltration using a semi-permeable membrane having a resolution rate between 10,000 and 30,000 daltons.

6. The process of claim 1 where step (c) comprises concentrating the microfiltration filtrate from step (a) or the ultrafiltration filtrate from step (b) by reverse osmosis.

7. The process of claim 1 where step (d) comprises countercurrent extracting the retentate at a pH between 1 and 3 with a water-immiscible organic solvent.

8. The process of claim 7 where the pH value of the retentate is adjusted with sulfuric acid.

9. The process of claim 8 where the retentate is extracted successively in a series of centrifugal extractors.

10. The process of claim 1 where the organic solvent is selected from ethyl acetate, methyl acetate, methyl isobutyl ketone, and n-butanol.

11. The process of claim 10 where the organic solvent is ethyl acetate.

12. The process of claim 1 where step (e) comprises drying the organic phase in vacuo using a rectification column.

13. The process of claim 12 where the organic phase is dried to a water content below 0.1%.

14. The process of claim 13 where the organic phase is dried to a water content between 0.03% and 0.05%.

15. The process of claim 1 where step (e) further comprises concentrating the organic phase.

16. The process of claim 1 further comprising decolorization of the organic phase.

17. The process of claim 15 where the decolorization is carried out with activated carbon.

* * * * *